US008543194B2

(12) United States Patent
Ting et al.

(10) Patent No.: US 8,543,194 B2
(45) Date of Patent: Sep. 24, 2013

(54) SYSTEM AND METHOD OF DETECTING ABNORMAL MOVEMENT OF A PHYSICAL OBJECT

(75) Inventors: Chuan-Wei Ting, Kaohsiung (TW); Ching-Yao Wang, Guiren Township (TW)

(73) Assignee: Industrial Technology Research Institute (TW)

(*) Notice: Subject to any disclaimer, the term of this patent is extended or adjusted under 35 U.S.C. 154(b) by 8 days.

(21) Appl. No.: 12/979,570

(22) Filed: Dec. 28, 2010

(65) Prior Publication Data

US 2012/0165691 A1    Jun. 28, 2012

(51) Int. Cl.
*A61B 5/04* (2006.01)
(52) U.S. Cl.
USPC .......................................................... 600/509
(58) Field of Classification Search
USPC .......................................................... 600/509
See application file for complete search history.

(56) References Cited

U.S. PATENT DOCUMENTS

| | | | |
|---|---|---|---|
| 2004/0122705 A1 | 6/2004 | Sabol et al. | |
| 2004/0122719 A1 | 6/2004 | Sabol et al. | |
| 2005/0288600 A1* | 12/2005 | Zhang et al. | 600/510 |
| 2007/0118399 A1 | 5/2007 | Avinash et al. | |
| 2009/0112106 A1* | 4/2009 | Zhang | 600/509 |
| 2009/0192394 A1 | 7/2009 | Guttag et al. | |
| 2009/0240157 A1* | 9/2009 | Lian et al. | 600/510 |
| 2010/0094152 A1 | 4/2010 | Semmlow | |

OTHER PUBLICATIONS

Aaronson, P.I. and Ward, J.P.T., The Cardiovascular System, 3rd Edition, Blackwell Publishing Ltd, Oxford, 2007.
Aysin, B. and Aysin, Elif, "Effect of Respiration in Heart Rate variability (HRV) Analysis," Proceedings of the 28th IEEE Engineering in Medicine and Biology Society, pp. 1776-1779, 2006.
Brennan, M., Palaniswami, M., and Kamen, P., "Do Existing Measures of Poincaré Plot Geometry Reflect Nonlinear Features of Heart Rate Variability," IEEE Transactions on Biomedical Engineering, 48, 11, pp. 1342-1347, 2001.
Costa, M., Goldberger, A.L., Peng, C.K., "Multiscale Entropy Analysis of Biological Signals", Physical Review, E 71,021906, 2005.
Costa, M., Peng, C.K., Goldberger, Ary L., "Multiscale Analysis of Heart Rate Dynamics: Entropy and Time Irreversibility Measures", Cardiovascular Engineering, pp. 88-93, 2008.

(Continued)

*Primary Examiner* — Niketa Patel
*Assistant Examiner* — William Levicky
(74) *Attorney, Agent, or Firm* — Lowe Hauptman & Ham, LLP

(57) ABSTRACT

The present application discloses a method of detecting abnormal movement of a physical object. A periodic signal is representative of the movement of the object. According to some embodiments, a raw matrix having a first array and a second array is generated, and then an integrated matrix is generated by performing a dimension reduction on the raw matrix. A likelihood of a predetermined type of abnormal movement of the physical object is determined by comparing the integrated matrix with a predetermined benchmark pattern. In some embodiments, the generation of the raw matrix includes performing a first analysis on a predetermined portion of the periodic signal to generate the first array and performing a second analysis different from the first analysis on the predetermined portion of the periodic signal to generate the second array.

12 Claims, 7 Drawing Sheets

(56) References Cited

OTHER PUBLICATIONS

Hansson-Sandsten, M. and Jönsson P., "Multiple Window Correlation Analysis of HRV Power and Respiratory Frequency," IEEE Transactions on Biomedical Engineering, 54, 10, pp. 1770-1779, 2007.

Khandoker, A.H., Jelinek, H.F., Palaniswami, M., "Heart rate Variability and Complexity in People with Diabetes Associated Cardiac Autonomic Neuropathy", Engineering in Medicine and Biology Society, pp. 4696-4699, 2008.

Lewis, Michael J., "Heart Rate Variability Analysis: A Tool to Assess Cardiac Autonomic Function," Computers, Information, Nursing, 23, pp. 335-341, 2005.

Piskorski, J. and Guzik, P., "Geometry of the Poincaré Plot of RR Intervals and its Asymmetry in Healthy Adults," Physiological Measurement, 28, pp. 287-300, 2007.

Risk, M., Bril, V., Broadbridge, C., Cohen, A., "Heart Rate Variability Measurement in Diabetic Neuropathy: Review of Methods", Diabetes Technology & Therapeutics, vol. 3, No. 1, pp. 63-76, 2001.

Rusu, L.D., Poantă, L., Hololeanu, C., Agoston, L.C., Zdrenghea, D., Dumitraşcu, D.L., "Heart Rate Variability Assessment—Physiological and Pathological Aspects", Automation, Quality and Testing, Robotics, pp. 57-59, 2008.

Thuraisingham, R.A. and Gottwald, G.A., "On Multiscale Entropy Analysis for Physiological Data," Physica A, 366, pp. 323-332, 2006.

Yang, Mingjing et al., "Mutual Information-Based Approach to the Analysis of Dynamic Electrocardiograms", Technology and Health Care 16 (2008) 367-375, IOS Press.

\* cited by examiner

SYSTEM AND METHOD OF DETECTING ABNORMAL MOVEMENT OF A PHYSICAL OBJECT

BACKGROUND

Some physical objects incorporate or encompass cyclic or periodic motion, such as an electrical motor having a rotor that spins at a rotational speed or a human heart beating (i.e., performing contraction and relaxation) at a heart rate. The cyclic movement of the physical objects is observable or recordable by detection systems in the form of periodic or substantially periodic signals. The term "periodic or substantially periodic signals" (hereinafter also referred to as "periodic signals") refers to the nature of the detected signals that usually have repetitive nominal waveform patterns although the exact waveforms and frequencies vary. Abnormal movement of a given physical object is thus detectable by analyzing the periodic signals.

For example, an Electrocardiograph (ECG) device is capable of converting the movement of a heart into one or more ECG signals from one or more combinations of leads attached to a person or animal undergoing examination. A trained medical care provider may identify certain abnormal movement(s) of the observed heart by comparing the ECG signals with a benchmark ECG signal of normal movement.

SUMMARY

In the present application, a method of detecting abnormal movement of a physical object is disclosed. According to some embodiments, a periodic signal is representative of movement of the physical object, and the method includes: generating a raw matrix comprising a first array and a second array; generating an integrated matrix by performing a dimension reduction on the raw matrix; and determining a likelihood of a predetermined type of abnormal movement of the physical object by comparing the integrated matrix or a set of indexes derived from the integrated matrix with a predetermined benchmark pattern corresponding to the predetermined type of abnormal movement.

In some embodiments, the generation of the raw matrix includes: performing a first analysis on a predetermined portion of the periodic signal to generate the first array, the predetermined portion corresponding to a predetermined time period of the periodic signal; and performing a second analysis different from the first analysis on the predetermined portion of the periodic signal to generate the second array.

In some embodiments, the first analysis or the second analysis is a time-domain analysis, a pattern analysis, or deriving a feature from the predetermined duration of the periodic signal obtained according to a first spatial measurement configuration and at least a portion of another periodic signal being representative of the movement obtained according to a second spatial measurement configuration.

In the present application, a method of detecting abnormality in a predetermined portion of an electrocardiography (ECG) signal corresponding to a predetermined time period is disclosed. In some embodiments, the method includes: segmenting the predetermined duration of ECG signal into a plurality of ECG segments, each ECG segment including a nominal ECG pattern; for adjacent ECG segments, re-sampling at least one of the adjacent ECG segments to derive two ECG arrays having the same number of data points; for adjacent ECG segments, calculating a joint probability and a marginal probability of the two ECG arrays of the adjacent ECG segments; generating a mutual information array based on the calculated joint probability and the calculated marginal probability of adjacent ECG segments; and determining a likelihood of a predetermined type of illness by comparing the mutual information array or a set of indexes derived from the mutual information array with a predetermined benchmark pattern corresponding to the predetermined type of illness.

In some embodiments, the calculation of the mutual information array is performed based on an equation of:

$$MI(X;Y) = \sum_x \sum_y p(x,y) \log \frac{p(x,y)}{p(x)p(y)}$$

where x and y each represents components of one of the two ECG arrays of the adjacent ECG segments, p(x,y) represents the joint probability of the two ECG arrays, and p(x) and p(y) each represents the marginal probability of one of the two ECG arrays of the adjacent ECG segments.

In the present application, an abnormality analysis system for performing the disclosed methods and computer readable storage medium being encoded with a computer program code which when executed by a processor causes the processor to perform the disclosed methods are also disclosed.

As will be realized, one or more embodiments are capable of other and different embodiments, and the several details are capable of modification in various obvious respects, all without departing from the described embodiments.

DESCRIPTION OF THE DRAWINGS

One or more embodiments are illustrated by way of example, and not by limitation, in the figures of the accompanying drawings, wherein elements having the same reference numeral designations represent like elements throughout and wherein.

DETAILED DESCRIPTION

Figure 1:
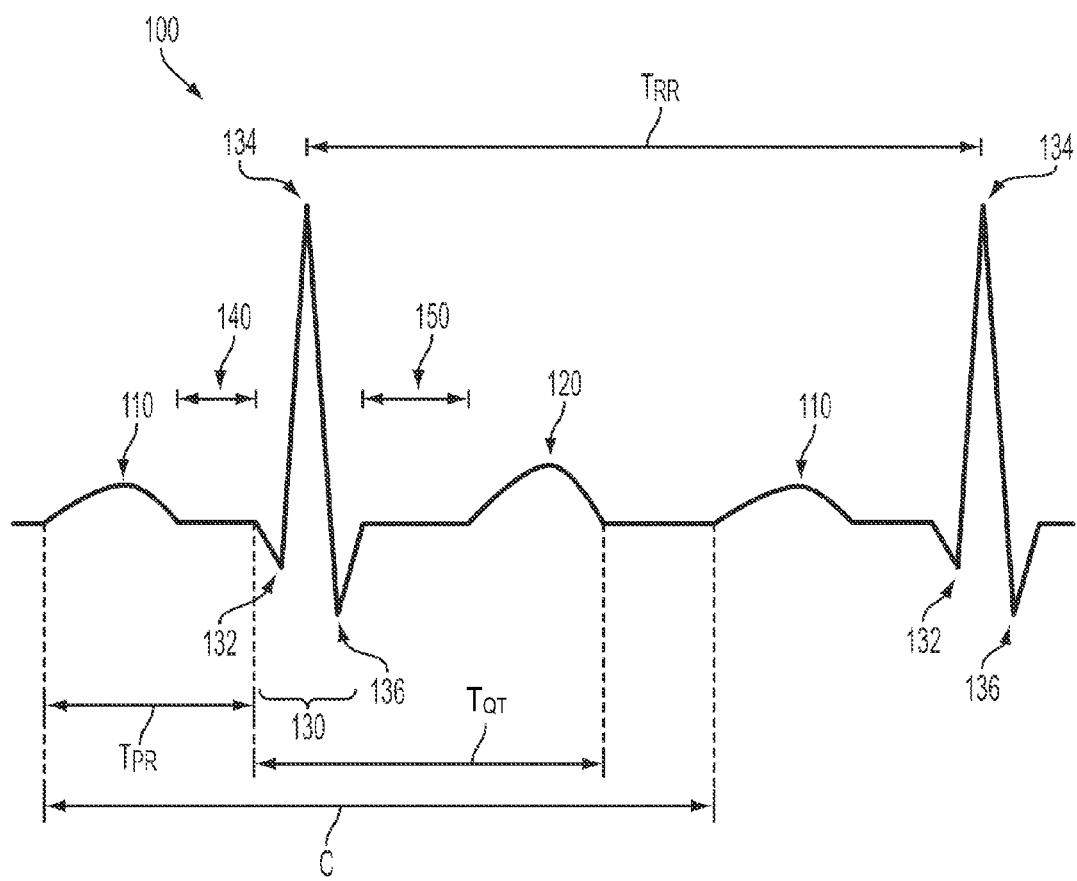
FIG. 1 is a plot of a waveform corresponding to an ECG signal.

FIG. 1 is a plot of a waveform 100 corresponding to an ECG signal of a human heart where the signal has been segmented and categorized into various segments (intervals) and feature points. Some of the segments and feature points of the ECG signal include P-wave 110, T-wave 120, QRS complex 130 that further includes a Q-point 132, an R-point 134, and an S-point 136, a PR-segment 140, and a ST-segment 150. A complete cardiac cycle C thus includes a P-wave 110 section, a PR-segment 140, a Q-point 132, an R-point 134, an S-point 136, a ST-segment 150, and a T-wave 120 section. In some embodiments, more segments and/or feature points are defined for various information processing purposes.

ECG signal sections and feature points are defined in order to facilitate the analysis of heart movement. In practice, illness or disease symptoms affect the rhythms or patterns of heart movement and are identifiable by analyzing ECG signal waveforms 100. Although the correlation between a given type of illness and the ECG signal waveforms 100 is usually identifiable, the given type of illness is more readily identifiable from resulting signals after performing a data analysis on ECG signal waveforms 100 particularly for emphasizing the correlation between a given illness type and the resulting signals.

Figure 2:
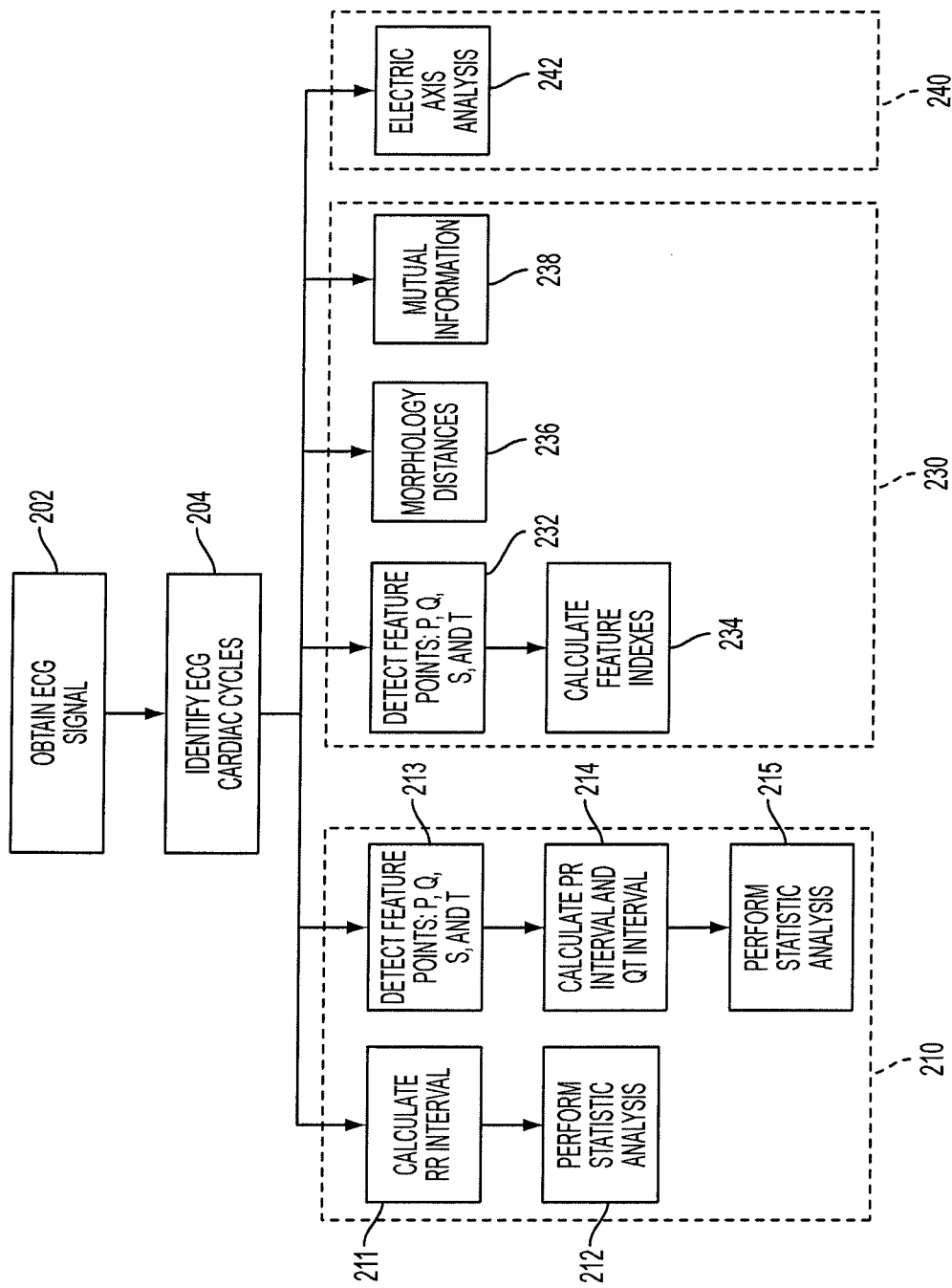
FIG. 2 is a flow chart of various methods of analyzing the waveform of the ECG signal of FIG. 1 in conjunction with some embodiments.

FIG. 2 is a flow chart of various example methods of analyzing the ECG signal. The process of performing an analysis on the ECG signal in order to generate resultant data is also referred to as feature extraction. In some embodiments, the disclosed analyses are performed by a computer system or an ECG equipment executing a software program, i.e., a set of executable/interpretable instructions. It is understood that in some embodiments only some of the disclosed analyses are performed for analyzing ECG signals for a patient. In some embodiments, a person having ordinary skill in the art will appreciate that additional operations are performed before, during, and/or after the method of FIG. 2.

In operation 202, an ECG signal such as the example signal depicted by waveform 100 in FIG. 1 is obtained through ECG transducers or stored ECG data transmitted from a storage device or via a network. Then, in operation 204, the cardiac cycles C of the ECG signal waveform 100 are identified. In some embodiments, the identification of cardiac cycles C includes first detecting some of the feature points. For example, in at least one embodiment, the cardiac cycles C of the ECG signal waveform 100 are identified according to detection of R-points 134 in the ECG signal waveform 100.

In some embodiments, at least one time-domain analysis 210 is performed on the ECG signal waveform 100. In at least one embodiment, after detection of R-points 134, the time intervals between two adjacent R-points (RR interval or RRI) $T_{RR}$ (FIG. 1) are calculated in operation 211. The RR intervals $T_{RR}$ represent the periods of cardiac cycles C (also referred to as NN intervals), i.e., the inverse information of a heart rate. Then, a statistical analysis is performed on the calculated RR intervals $T_{RR}$ in operation 212. In some embodiments, the calculated RR intervals $T_{RR}$ are analyzed according to one or more of the following approaches: standard deviation of NN intervals (SDNN), standard deviation of average NN intervals (SDANN), the root-mean-square of successive differences of RR intervals (RMSSD), the number of pairs of successive NN intervals that differ by more than 50 ms (NN50), the proportion of NN50 divided by total number of NN intervals (pNN50), etc.

In at least another embodiment, after detection of R-points 134, other feature points and sections, such as Q-points 132, S-points 136, P-wave 110, and T-wave 120, are also detected in operation 213. Then, PR intervals $T_{PR}$ (FIG. 1) and QT intervals $T_{QT}$ (FIG. 1) are calculated in operation 214, and either one or both of these two intervals are informative features for representing characteristics of a cardiac cycle C. Finally, in operation 215, a statistical analysis similar to the methods described above for operation 212 is performed on the calculated PR intervals $T_{PR}$, and the QT intervals $T_{QT}$.

In some embodiments, at least one morphology analysis 230 is performed on the ECG signal waveform 100. A morphology analysis refers to an analysis based on the waveforms or patterns of the examined signal. In at least one embodiment, after detection of R-points 134, other feature points and sections, such as Q-points 132, S-points 136, P-wave 110, and T-wave 120, are also detected and identified in operation 232. Subsequently in operation 234, features such as slopes of ST segment 150, T-wave 120, P-wave 110, or other features are derived from the variance of patterns of recorded cardiac cycles C.

In at least one embodiment, in operation 236, the morphology analysis 230 includes extracting features derived from the variance between adjacent cardiac cycles C of the ECG signal waveform 100. In at least another embodiment, the morphology analysis 230 performed in operation 238 includes a method of evaluating morphology variance between two adjacent cardiac cycles C of the ECG signal waveform 100 by calculating mutual information based on joint and marginal probabilities.

In some embodiments, one or more other types of analyses 240 are performed on the ECG signal waveform 100. For example, in some embodiments after detection of R-points 134, features concerning electrical axis of a heart are calculated in operation 242 based on positive/negative waves at feature points (such as P-wave 110, Q-point 132, R-point 134, S-point 136, T-wave 120, etc.) from ECG signals received from a different combination of leads.

Figure 3:
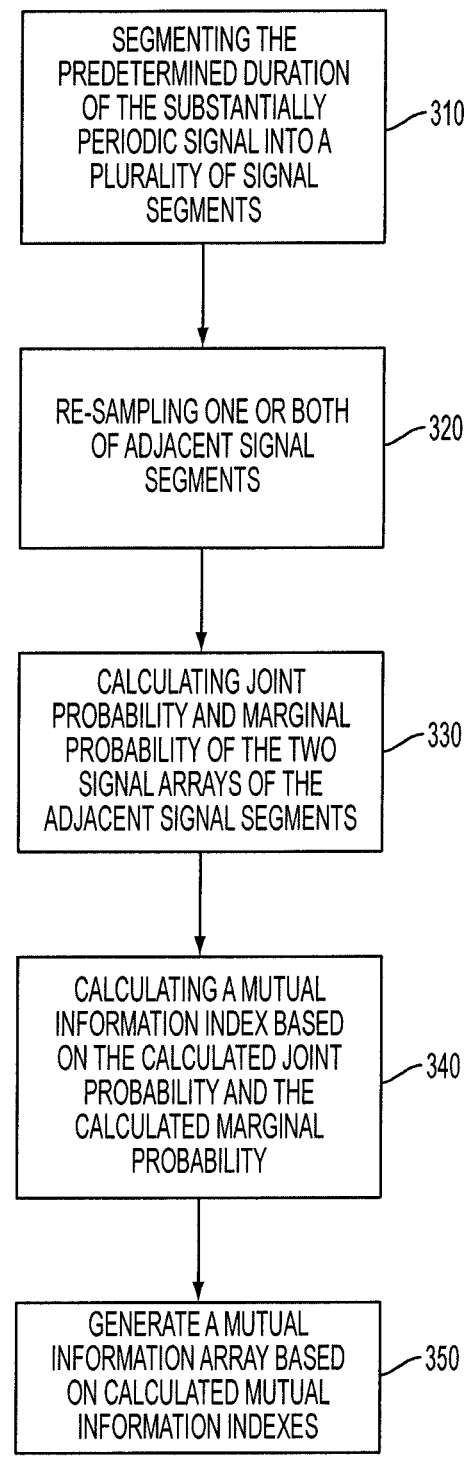
FIG. 3 is a flow chart of a method of analyzing periodic signals representing movement of a physical object according to some embodiments.

FIG. 3 is a flow chart of a method of analyzing periodic signals representing movement of a physical object according to some embodiments. The analysis method depicted in FIG. 3 is a method based upon morphology of the examined substantially periodic signal, such as the ECG signal waveform 100 analyzed according to operation 238 in FIG. 2. It is understood that in some embodiments additional operations are performed before, during, and/or after the method of FIG. 3.

In operation 310, a predetermined portion of the substantially periodic signal corresponding to a predetermined time period is segmented into a plurality of signal segments, each signal segment including a nominal waveform. For example, in at least one embodiment for which a predetermined duration of the ECG signal waveform 100 is being analyzed, the nominal waveform is the waveform pattern corresponding to a cardiac cycle C, and the segmentation is performed by dissecting the ECG signal waveform 100 in between adjacent R-points. In some embodiments, the nominal waveform is the waveform defined between adjacent R-points 134, and the segmentation is performed by dissecting the ECG signal waveform 100 at R-points 134.

The analyzed substantially periodic signal, such as an ECG signal waveform 100 in some embodiments, is a discrete-time signal and thus the signal segments are also sequences of data points or data arrays. However, because the effective frequency of the analyzed substantially periodic signal varies even within the time period of the predetermined portion of the substantially periodic signal, the size of the signal segments is not necessarily the same. Therefore, in operation 320, two signal arrays in adjacent signal segments having the same size are obtained by re-sampling one or both of the adjacent signal segments. "Re-sampling" refers to re-creation of a continuous waveform based on an original data array and deriving a new data array from the re-created continuous waveform, and thus the new data array and the original data array both represent the same continuous waveform. In some embodiments, the re-sampling is performed by interpolation or extrapolation of the original data array in a linear or polynomial manner or other applicable curve-fitting algorithms.

For example, in some embodiments, one of two signal segments corresponding to neighboring cardiac cycles C are re-sampled in order to generate two corresponding signal arrays having the same size. If, for example, after segmentation, a first cardiac cycle C includes 262 data points, and a second cardiac cycle C includes 274 data points, either one of the first cardiac cycle or the second cardiac cycle is re-sampled to match the size, i.e., same number of data points, of the other cardiac cycle. In some embodiments, the second cardiac cycle is re-sampled to generate a signal array having the same size as the first cardiac cycle, e.g., said 262 data points.

In operation 330, after the re-sampling for adjacent signal segments the joint probability and the marginal probability of the two signal arrays of the adjacent signal segments are calculated. In some embodiments, the joint probability and marginal probability are calculated according to the two re-sampled signal arrays X and Y of ECG signals of adjacent periods (i.e., adjacent signal segments corresponding to neighboring cardiac cycles C). Elements of the signal array X or signal array Y represent magnitudes of the ECG signals. The marginal probability of each signal array (X or Y) is determined by first accumulating the counts of each different value of elements in the signal array, and then calculating the proportion of each cumulative count to the total amount of elements in the signal array to obtain the marginal probabilities of each different value of elements p(x) or p(y). Considering both sequences X and Y together, similar to the calculation of marginal probability, the joint probability p(x,y) of two events x and y in conjunction is determined. Then, in operation 340, a mutual information index is calculated based on the calculated joint probability and the calculated marginal probability of every adjacent signal segments. In at least one embodiment, the calculation of the mutual information index is performed based on application of the following equation:

$$MI(X;Y) = \sum_x \sum_y p(x,y) \log \frac{p(x,y)}{p(x)p(y)}$$

X and Y represent components of one of the two signal arrays of the adjacent signal segments, p(x,y) represents the joint probability of the two signal arrays, and p(x) and p(y) each represents the marginal probability of one of the two signal arrays of the adjacent signal segments.

In operation 350, a mutual information array is generated based on the calculated mutual information indexes. For example, the mutual information array includes an array of the calculated mutual information indexes listed based on their sequence in the examined ECG signal waveform 100. The generated mutual information array is usable for further information processing. In at least one embodiment, the generated mutual information array is compared with a predetermined benchmark pattern corresponding to one or more predetermined types of illness in order to determine the likelihood of the one or more corresponding predetermined types of illness.

Although the method depicted in FIG. 3 is explained using ECG signals as an example, a person having ordinary skill in the art will appreciate that the same analysis method is usable for analyzing substantially periodic signals other than ECG signals. In some embodiments, the substantially periodic signal to be analyzed is obtained by detecting one of the following activities: heartbeat, breathing, speech, earthquake or seismic activity, orbital movement of an astronomical object, periodic variances of an astronomical object, movement of a piston, or rotation of a motor. Also, the analysis method of FIG. 3 is usable to detect a likelihood of a predetermined type of abnormal movement of the physical object by comparing the mutual information matrix with a predetermined benchmark pattern corresponding to the predetermined type of abnormal movement.

Figure 4:
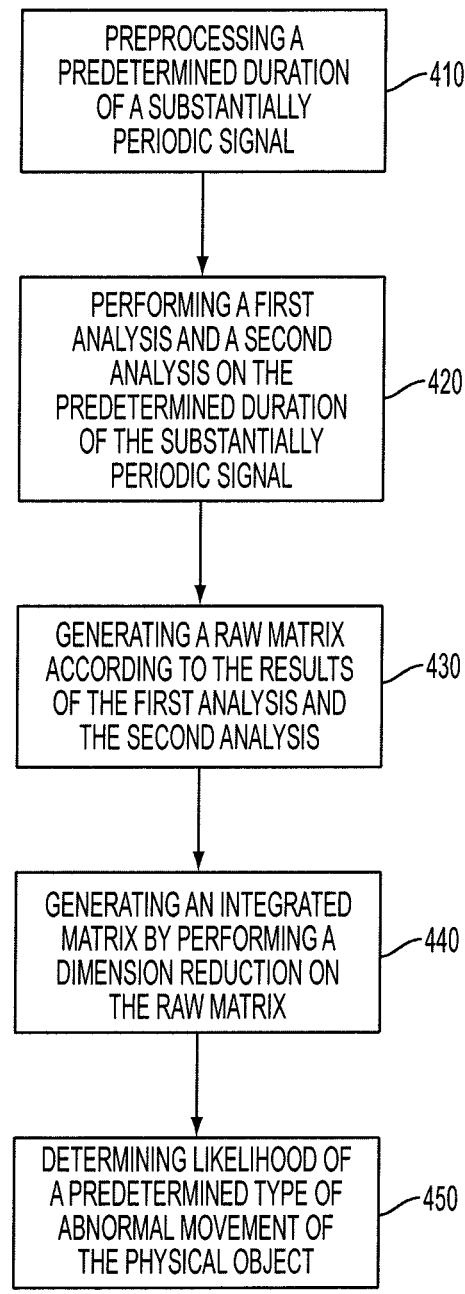
FIG. 4 is a flow chart of a method of detecting abnormal movement of a physical object according to some embodiments.

FIG. 4 is a flow chart of a method of detecting abnormal movement of a physical object according to some embodiments. The method depicted in FIG. 4 is explained in the context of analyzing an ECG signal waveform 100 as depicted in FIG. 1. It is understood that, in some embodiments, the method depicted in FIG. 4 is usable for analyzing various types of periodic signals representing movement of a physical object. A person having ordinary skill in the art will appreciate that in some embodiments additional operations are performed before, during, and/or after the method of FIG. 4.

In general, the method depicted in FIG. 4 incorporates results from two or more different analyses or feature extraction methods, such as the ones disclosed in FIG. 2, into an integrated feature matrix in order to consolidate information for further analysis, such as risk assessment based on an ECG signal or abnormal movement detection of a physical object, while reducing the total amount of data.

In operation 410, a predetermined portion of a substantially periodic signal is obtained and pre-processed. In at least one embodiment for analyzing an ECG signal, a predetermined period of ECG signals is obtained by an ECG transducer to record electrical potential difference of heart muscle cells caused by electrical pulses of a heart that is being observed. In some embodiments, more ECG transducers or the same transducer with leads attached to different portions of a human body are, used to provide electrical axis information or other information. In yet some other embodiments where other biological or non-biological signals are to be analyzed, applicable detecting systems or transducers other than ECG transducers are used.

In some embodiments, the detected ECG signal is further amplified and/or level-shifted to have signal levels of the ECG signal adjusted to be within a predetermined range for further analog-to-digital conversion and/or filtering. In at least one embodiment, the detected ECG signals are also affected by breathing or factors not relevant to the heart activities. Therefore, the contribution of noise or other component in the detected ECG signal from irrelevant factors is suppressed in order to obtain a filtered ECG signal, such as the example ECG signal depicted in FIG. 1, for subsequent information processing.

After obtaining the predetermined portion of the substantially periodic signal to be analyzed, a raw matrix comprising at least two data arrays derived based on different signal analyses is generated.

For example, in operation 420, a first analysis is performed on the predetermined portion of the substantially periodic signal to generate a first array, and a second analysis different from the first analysis is performed on the predetermined portion of the substantially periodic signal to generate a second array. In some embodiments, more than two different analyses are performed and more than two resulting data arrays are generated.

In some embodiments analyzing a non-ECG signal, the first analysis or the second analysis is a time-domain analysis, a morphology analysis, a pattern analysis, or derivation of a feature from the predetermined duration of the substantially periodic signal obtained according to a first spatial measurement configuration and at least a portion of another substantially periodic signal is representative of the movement obtained according to a second spatial measurement configuration.

In some other embodiments analyzing an ECG signal waveform 100, the first analysis or the second analysis is a time-domain analysis, a morphology analysis, an electric-axis analysis. For example, two or more of the following analysis are performed: RR Interval analysis (e.g., operations 211/212), PR-QT interval analysis (e.g., operation 213/214/215), morphology feature analysis (e.g., operation 232/234), morphology distance analysis (e.g., operation 236), mutual information analysis (e.g., method depicted in FIG. 3), electric axis analysis (e.g., operation 242), or other available ECG signal analyses.

In operation 430, a raw matrix is generated according to the results of the analysis performed on the periodic signal, such as the first analysis and the second analysis selected from one of the ECG signal analysis methods depicted in FIGS. 2 and 3, as well as other applicable ECG or biology signal analysis methods. In some embodiments, results from a third or more different analyses are incorporated in the raw matrix.

Subsequently in operation 440, an integrated feature matrix having a dimension no greater than the dimension of the raw matrix is generated by performing a dimension reduction on the raw matrix. In some embodiments, the dimension reduction is performed by applying principal component analysis, factor analysis, or independent component analysis on the raw matrix.

In operation 450, the likelihood of a predetermined type of abnormal movement of the physical object is determined by comparing the integrated matrix with a predetermined benchmark pattern corresponding to the predetermined type of abnormal movement. For example, if ECG signals of a heart are analyzed, the abnormal activities of the heart being examined are identified, and the likelihood of a predetermined type of illness correlated to the abnormal activities is assessed accordingly.

Although the method depicted in FIG. 4 is explained with reference to analyzing ECG signals, the same analysis method is usable for analyzing substantially periodic signal other than ECG signals. In some embodiments, the substantially periodic signal to be analyzed is obtained by detecting one of the following activities: heartbeat, breathing, speech, earthquake or seismic activity, orbital movement of an astronomical object, periodic variances of an astronomical object, movement of a piston, or rotation of a motor. Also, the analysis method of FIG. 4 is usable to detect likelihood of a predetermined type of abnormal movement of the physical object by comparing the integrated feature matrix with a predetermined benchmark pattern corresponding to the predetermined type of abnormal movement.

For example, in some embodiments that analyze a predetermined duration of speech for recognizing the acoustic characters of the speech, the predetermined duration of speech signal is segmented into a plurality of windows, and each window includes one or more periods of speech waveforms. The mutual information analysis method of FIG. 3 is usable to obtain a mutual information array representing the variations among different windows. Further, together with data arrays derived by using other analysis methods such as the ones similar to the methods depicted in blocks 210/230/240 of FIG. 2, an integrated matrix is derived using the method of FIG. 4 in order to suppress noises for subsequent speech processing.

Figure 5:
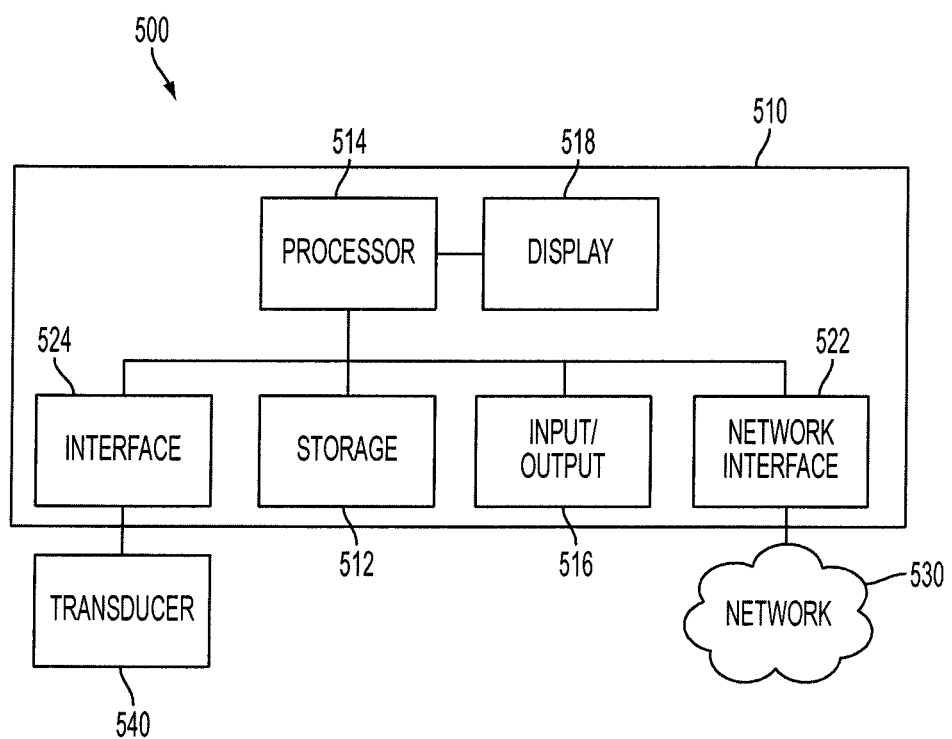
FIG. 5 is a functional block diagram of an abnormality analysis system usable for implementing the method disclosed in FIGS. 2-4 according to some embodiments.

FIG. 5 is a functional block diagram of an abnormality analysis system usable for implementing the method disclosed in FIGS. 2-4 according to some embodiments.

Abnormality analysis system 500 includes a computer system 510 comprising a computer readable storage medium 512 encoded with, i.e., storing, a computer program code, i.e., a set of executable instructions. The computer system 510 includes a processor 514 electrically coupled to the computer readable storage medium 512. The processor 514 is configured to execute or interpret the computer program code encoded in the computer readable storage medium 512 in order to cause the computer to function as a signal analyzer for performing the abnormality analysis and risk assessment for the substantially periodic signal to be examined, such as an ECG signal, as depicted in FIGS. 2-4.

In some embodiments, the processor 514 is a central processing unit (CPU), a multi-processor, a distributed processing system, and/or any suitable processing unit. In at least one embodiment, the processor 514 acquires information such as the predetermined duration of periodic signal, the predetermined benchmark pattern, and/or other information from the memory storage medium 512.

In some embodiments, the computer readable storage medium 512 is an electronic, magnetic, optical, electromagnetic, infrared, and/or a semiconductor system (or apparatus or device). For example, the computer readable storage medium 512 includes a semiconductor or solid-state memory, a magnetic tape, a removable computer diskette, a random access memory (RAM), a read-only memory (ROM), a rigid magnetic disk, and/or an optical disk. In some embodiments using optical disks, the computer readable storage medium 512 includes a compact disk-read only memory (CD-ROM), a compact disk-read/write (CD-R/W), and/or a digital video disc (DVD).

Further, the computer system 510 includes an input/output interface 516 and a display 518. The input/output interface 516 is coupled to the processor 514 and allows an operator or a medical care professional to operate the computer system 510 in order to perform the methods depicted in FIGS. 2-4. The display 518 displays the status of operation of the methods depicted in FIGS. 2-4 in a real-time manner, and preferably provides a Graphical User Interface (GUI). The input/output interface 516 and the display 518 allow an operator to operate the computer system 512 in an interactive manner.

The computer system 510 also includes a network interface 522 coupled to the processor 514. The network interface 522 allows the computer system 510 to communicate with a network 530, to which one or more other computer systems are connected. The network interface 522 includes wireless network interfaces such as BLUETOOTH, WIFI, WIMAX, GPRS, or WCDMA; or wired network interface such as ETHERNET, USB, or IEEE-1394. In some embodiments, the method of FIGS. 2-4 are implemented in two or more computer systems 510 of FIG. 5, and information such as the predetermined duration of periodic signal, the predetermined benchmark pattern, and/or other information are exchanged between different computer systems via the network 530.

In at least one embodiment, the abnormality analysis system 500 further comprises a transducer 540. The transducer 540 is capable of observing the physical object to be examined and converting the movement of the physical object into a representative signal. In some embodiments analyzing ECG signals, the transducer 540 observes the heart to be examined and converts the muscle movement of the heart into ECG signals.

The computer system 510 further has an interface 524 coupled to the transducer 540 and the processor 514. The interface 524 bridges the transducer 540 with the processor 514 and outputs the picked up periodic signals in discrete-time signal format. For example, if the transducer 540 picks up an ECG signal, the interface receives the ECG signal from the transducer 540 and outputs the ECG signal in the format of a ECG data array to the processor 514. In some embodiments, the transducer 540 converts one of the following physical phenomenon into electrical signals: heartbeats, breathing, speech, earthquakes, orbital movement of an astronomical object, periodic variances of an astronomical object, movement of a piston, or rotation of a motor.

Figure 6A:
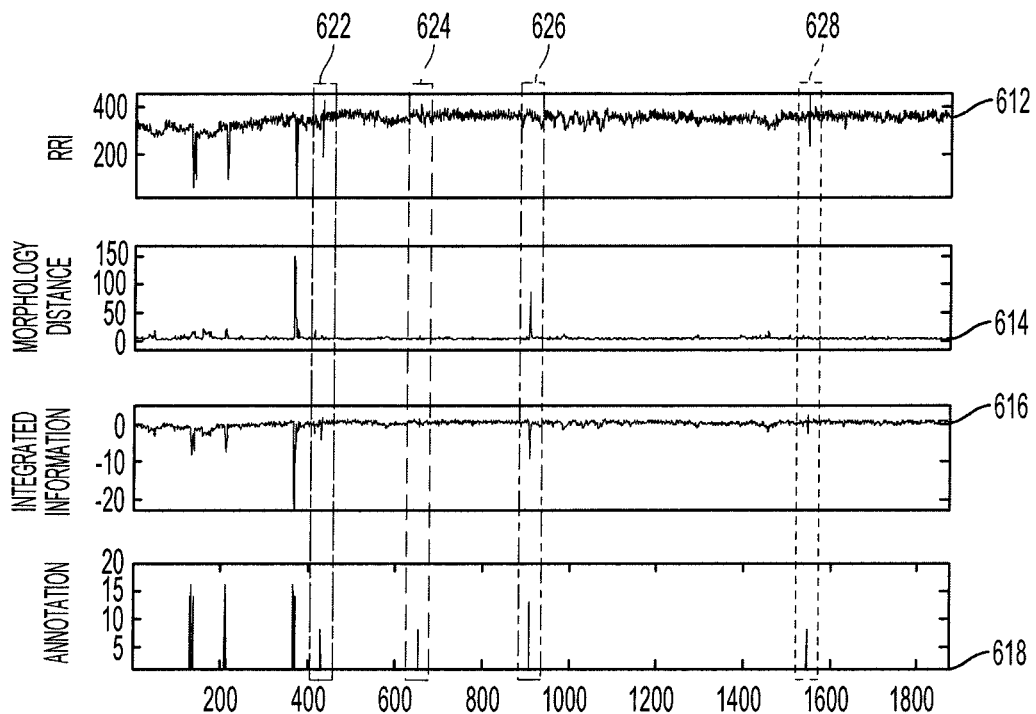
FIGS. 6A and 6B are charts of resulting data arrays of various analyses performed on a benchmark ECG signal, integrated matrices, and an annotated waveform corresponding to abnormal movement according to some embodiments.

FIG. 6A is a chart of resulting data arrays 612/614 of two different analyses performed on a benchmark ECG signal representing abnormal movement of a heart, an integrated matrix 616 according to the results of the two different analyses, and an annotated waveform 618 identifying windows 622~628 for pulses corresponding to abnormal movement according to some embodiments.

The example depicted in FIG. 6A uses at least two different ECG feature extraction methods: time-domain RR Interval analysis and morphology distance analysis. The testing is performed based on arrhythmia database of Massachusetts Institute of Technology and Boston's Beth Israel Hospital (MIT-BIH), which is an international standard database. Comparing the result of RR Interval analysis 612 with the annotated waveform 618, application of the RR Interval analysis on the examined ECG signal reveals abnormal movement corresponding to the abnormality identified at windows 622 and 628. However, the result of RR Interval analysis 612 fails to identify the abnormal movement corresponding to the abnormality identified at windows 624 and 626. In the same example, the result of morphology distance analysis 614, compared with the annotated waveform 618, reveals abnormal movement corresponding to the abnormality identified at windows 626. However, the result of morphology distance analysis 614 fails to identify the abnormal movement corresponding to the abnormality identified at windows 622, 624, and 628.

After information integration and dimension reduction in accordance with the method depicted in FIG. 4, the information relevant to identifying abnormal movement corresponding to the abnormality identified at windows 622, 626, and 628 from resulting arrays 612 and 614 are integrated into the integrated feature matrix 616. In at least one embodiment, the integrated feature matrix 616 is a one-by-N array derived from a raw matrix, which is a two-by-N matrix including two one-by-N arrays (the resulting arrays 612 and 614). N is the number of data points in the resulting arrays 612 and 614.

Therefore, a single integrated feature matrix 616 is usable for identifying the abnormality identifiable by the resulting arrays 612 and 614. That is, the integrated matrix 616 integrates and preserves information in the resulting arrays 612 and 614 relevant to subsequent abnormality detection while reducing the overall volume of information, and thus to improve the computation efficiency in subsequent determination of abnormal movement.

Figure 6B:
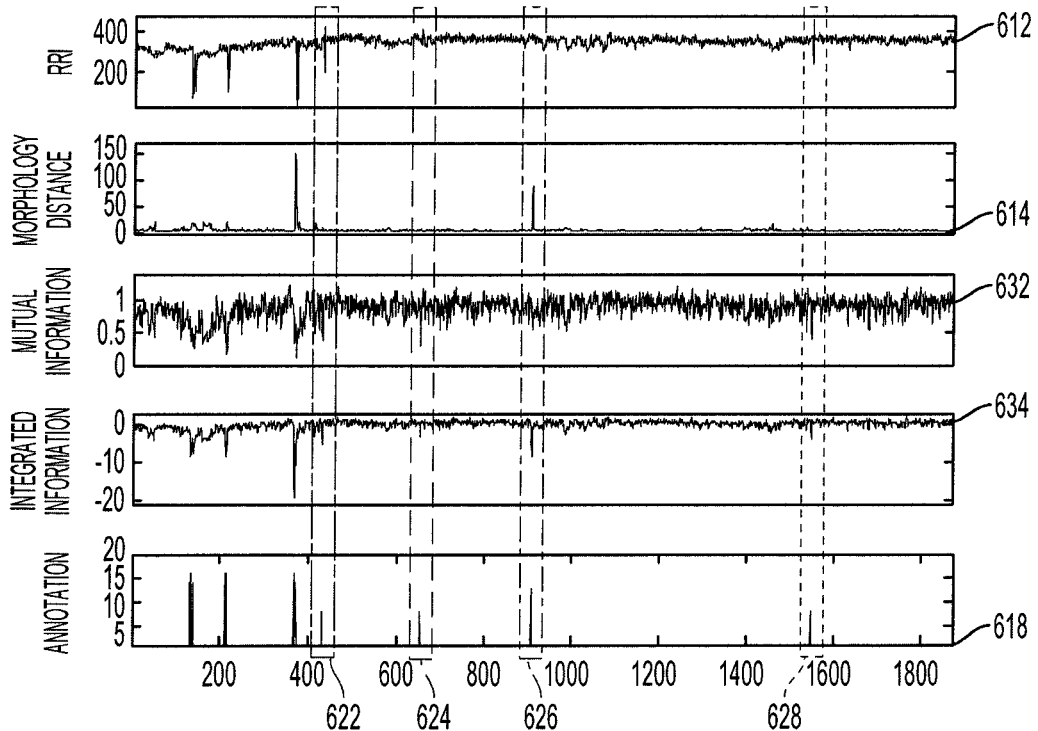

FIG. 6B is a chart of resulting data arrays 612/614/632 of three different analyses performed on a benchmark ECG signal representing abnormal movement of a heart, an integrated matrix 634 according to the results of the three different analyses, and an annotated waveform 618 identifying windows 622~628 for pulses corresponding to abnormal movement according to some embodiments. The testing is also performed based on the MIT-BIH arrhythmia database. In addition to the results of RR Interval analysis 612 and morphology distance analysis, the resulting data array 632 is derived based on mutual information analysis as depicted in FIG. 3. Compared with the annotated waveform 618, applying mutual information analysis reveals abnormal movement corresponding to the abnormality identified at windows 622 and 628, and also at window 624, which is not easily detectable from solely the results of RR Interval analysis 612 and morphology distance analysis 614. Although, the result of mutual information analysis 632 fails to identify the abnormal movement corresponding to window 626, mutual information analysis helps to remedy the deficiencies of the RR Interval analysis and the morphology distance analysis.

After information integration and dimension reduction as depicted in FIG. 4, the information relevant to identifying positions 622, 624, 626, and 628 from resulting arrays 612, 614, and 632 are integrated into the integrated feature matrix 634. In at least one embodiment, the integrated feature matrix 634 is a one-by-N array derived from a raw matrix, which is a three-by-N matrix including three one-by-N arrays (the results 612, 614, and 632). N being the number of data points in the resulting data arrays 612, 614, and 632. Therefore, a single integrated feature matrix 634 is usable for identifying the abnormal movement identifiable by the resulting arrays 612, 614, and 632 by using a reduced-size matrix. That is, the integrated feature matrix 634 integrates and preserves information relevant to subsequent abnormality detection while reducing the overall volume of information, and thus to improve the computation efficiency in subsequent determination of abnormal movement.

Figure 7A:
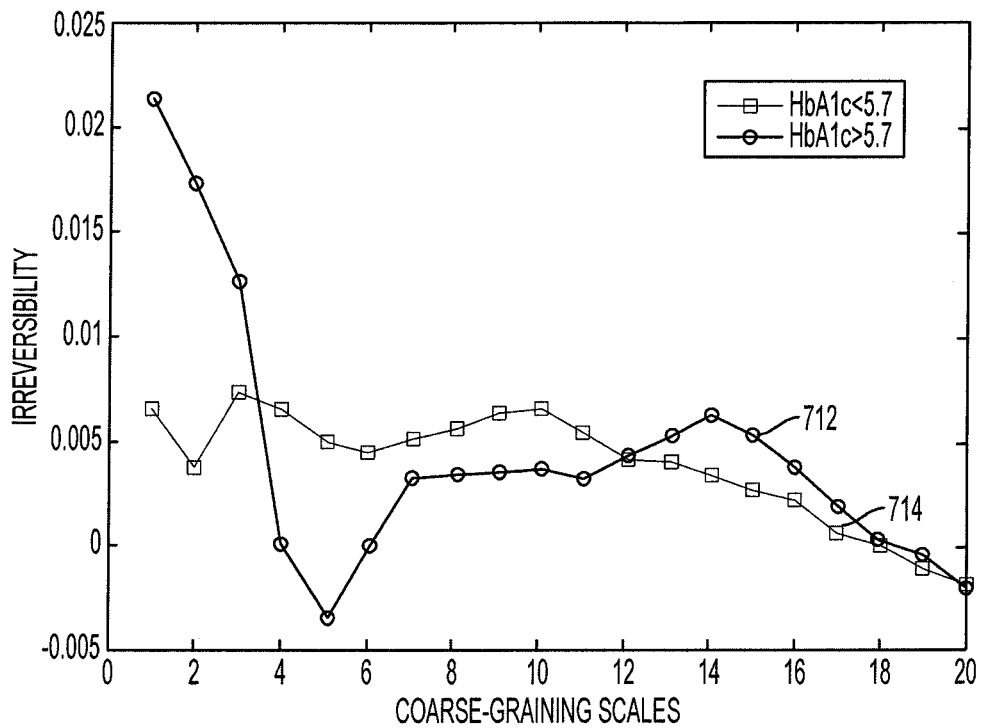
FIGS. 7A and 7B are charts of resulting data arrays of performing asymmetric index (AI) of multi-scale analysis on results of RR interval analysis and an integrated matrix derived from ECG signals of end-stage renal disease (ESRD) patients according to some embodiments.

FIG. 7A is a chart of resulting data arrays of performing asymmetric index (AI) of multi-scale analysis on results of RR interval analysis of ECG signals obtained from observing End Stage Renal Disease (ESRD) patients, with or without diabetes mellitus (DM), according to some configurations. It is known to the applicants that ESRD patients' conditions regarding DM are discernable by Glycated hemoglobin (HbA1c) tests. While ESRD patients with DM demonstrate HbA1c greater than 5.7, ESRD patients without DM demonstrate HbA1c less than 5.7. As depicted in FIG. 7A, results of performing the AI analysis based on results of RR interval analysis for ESRD patients with DM 712 and ESRD patients without DM 714 are not helpful in distinguishing these two different groups.

Figure 7B:
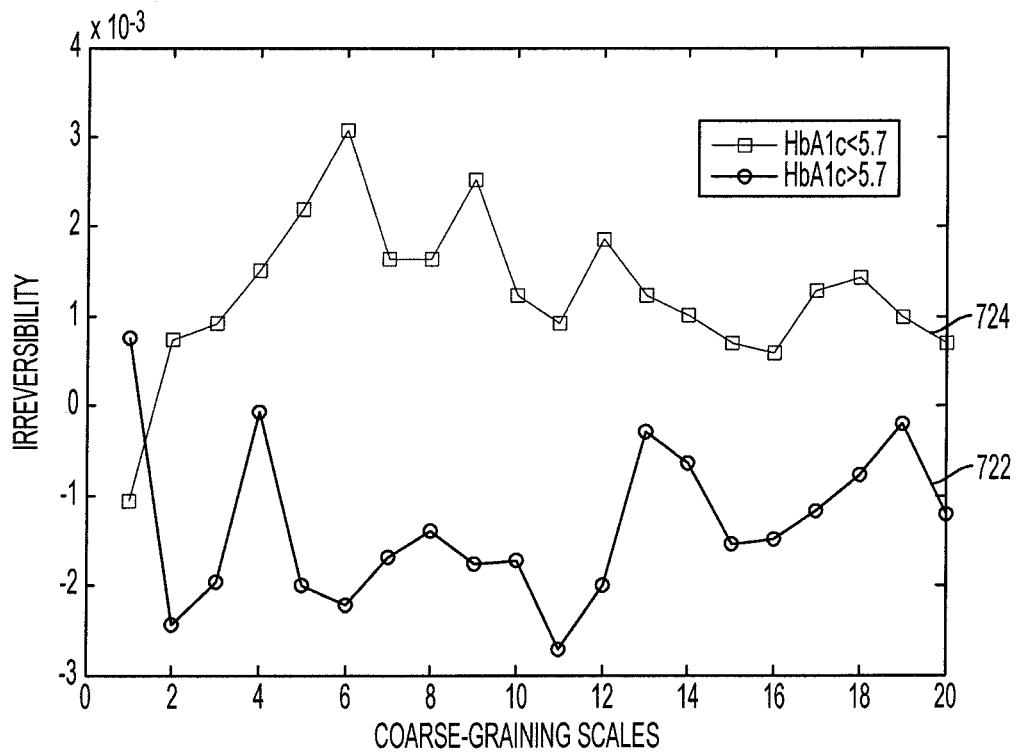

FIG. 7B is a chart of resulting data arrays of performing AI of multi-scale analysis on an integrated feature matrix based on results of RR interval analysis, morphology distance analysis and mutual information analysis of ECG signals obtained from observing ESRD patients, with or without DM, according to some embodiments. As depicted in FIG. 7B, results of performing the AI based on results of integrated matrix for ESRD patients with DM 722 and without DM 724 fall in different ranges, and thus the analysis is helpful in distinguishing these two different groups. Thus, compared with performing analysis depicted in FIG. 2 individually, in some embodiments, the analysis method as depicted in FIG. 4 not only incorporates information from various analyses, but also enhances the correlation between the results of the analysis, i.e., the integrated feature matrix, and one or more patterns corresponding to particular illness or abnormality. Moreover, compared with tests that require blood-drawing and days of laboratory test, analyzing ECG signals is a relatively less invasive and more time-efficient approach in distinguishing ESRD patients with and without DM.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A method of detecting abnormality in a predetermined portion of an electrocardiography (ECG) signal corresponding to a predetermined time period, the method comprising:
   segmenting the predetermined duration of ECG signal into a plurality of ECG segments, each ECG segment including a nominal ECG pattern, and the plurality of ECG segments including one or more pairs of adjacent ECG segments;
   for each pair of the one or more pairs of adjacent ECG segments:
      re-sampling at least one of the adjacent ECG segments to derive two ECG arrays having the same number of data points representative of magnitude of waveforms of the adjacent ECG segments; and
      calculating a joint probability and a marginal probability of the two ECG arrays of the adjacent ECG segments;
   generating a mutual information array based on the calculated joint probability and the calculated marginal probability of the one or more pairs of adjacent ECG segments; and
   determining a likelihood of a predetermined type of illness by comparing the mutual information array or a set of indexes derived from the mutual information array with a predetermined benchmark pattern corresponding to the predetermined type of illness.

2. The method of 1, wherein the calculation of the mutual information array is performed based on an equation of:

$$MI(X;Y) = \sum_x \sum_y p(x, y) \log \frac{p(x, y)}{p(x)p(y)}$$

where x and y each represents components of one of the two ECG arrays of the adjacent ECG segments, p(x,y) represents the joint probability of the two ECG arrays, and p(x) and p(y) each represents the marginal probability of one of the two ECG arrays of the adjacent ECG segments.

3. The method of 1, further comprising:
   performing a first analysis different from the generation of the mutual information array on the predetermined duration of ECG signal to generate a first array; and
   generating an integrated matrix by performing a dimension reduction on a raw matrix comprising the mutual information array and the first analyzed array.

4. The method of claim 3, wherein the first analysis is a time-domain analysis, a morphology analysis, or an electric-axis analysis.

5. The method of claim 3, wherein the dimension reduction is performed by applying principal component analysis, factor analysis, or independent component analysis on the raw matrix.

6. The method of claim 3, further comprising:
   performing a second analysis different from the generation of the mutual information array on the predetermined duration of ECG signal and the first analysis on the predetermined duration of ECG signal array to generate a second array;
   wherein the raw matrix comprising the mutual information array, the first array, and the second array.

7. An abnormality analysis system comprising:
   a computer readable storage medium encoded with a computer program code;
   a processor coupled to the computer readable storage medium, the processor being configured to execute the computer program code;
   wherein the computer program code is configured to cause the processor to:
      receive an electrocardiography (ECG) data array representing a predetermined duration of activity of a heart;
      divide the ECG data array into a plurality of ECG segments, each ECG segment including a nominal ECG waveform, and the plurality of ECG segments including one or more pairs of adjacent ECG segments;
      for each pair of the one or more pairs of adjacent ECG segments:
         derive two same-size ECG arrays representative of magnitude of waveforms of the adjacent ECG segments by re-sampling one or both of the adjacent ECG segments; and
         calculate joint probability and marginal probability of the two same-size ECG arrays of the adjacent ECG segments;
      generate a mutual information array based on the calculated joint probability and the calculated marginal probability of the one or more pairs of adjacent ECG segments; and
      determine likelihood of abnormal movement of the heart by comparing the mutual information array or a set of indexes derived from the mutual information array with a predetermined benchmark pattern.

8. The abnormality analysis system of claim 7, wherein the computer program code is further configured to cause the processor to:
   perform a first analysis different from the generation of the mutual information array on the ECG data array to generate a first array; and
   generate an integrated matrix by performing a dimension reduction on a raw matrix comprising the mutual information array and the first array.

9. The abnormality analysis system of claim 7, further comprising:
   a transducer configured to observe the heart; and
   an interface coupled to the transducer and the processor and configured to output the ECG data array to the processor.

10. The abnormality analysis system of claim 7, further comprising:
    a network interface coupled to the processor and a network;
    wherein the computer program code is configured to cause the processor to receive the predetermined benchmark pattern transmitted from the computer readable storage medium or the network.

11. A computer readable storage medium being encoded with a computer program code which when executed by a processor causes the processor to perform a method comprising:
    receiving an electrocardiography (ECG) data array representing a predetermined duration of activity of a heart;
    dividing the ECG data array into a plurality of ECG segments, each ECG segment including a nominal ECG waveform, and the plurality of ECG segments including one or more pairs of adjacent ECG segments;

for each pair of the one or more pairs of adjacent ECG segments:
  deriving two same-size ECG arrays representative of magnitude of waveforms of the adjacent ECG segments by re-sampling one or both of the adjacent ECG segments; and
  calculating joint probability and marginal probability of the two same-size ECG arrays of the adjacent ECG segments;
generating a mutual information array based on the calculated joint probability and the calculated marginal probability of the one or more pairs of adjacent ECG segments; and
determining a likelihood of abnormal movement of the heart by comparing the mutual information array or a set of indexes derived from the mutual information array with a predetermined benchmark pattern.

12. The computer readable storage medium of claim 11, wherein the computer program code is further configured to cause the processor to:
  perform a first analysis different from the generation of the mutual information array on the predetermined duration of ECG signal to generate a first array; and
  generate an integrated matrix by performing a dimension reduction on a raw matrix comprising the mutual information array and the first array.

* * * * *